(12) United States Patent
Allerdings et al.

(10) Patent No.: US 10,789,500 B2
(45) Date of Patent: *Sep. 29, 2020

(54) SUPPLEMENTAL DEVICE FOR ATTACHMENT TO AN INJECTION DEVICE FOR RECORDING AND DISPLAYING A DOSE VALUE SET BY THE USER USING OPTICAL CHARACTER RECOGNITION (OCR)

(71) Applicant: Sanofi-Aventis Deutschland GmbH, Frankfurt am Main (DE)

(72) Inventors: Alexander Allerdings, Frankfurt am Main (DE); Christian Hoffmann, St. Polten (AT); Rainer Fischer, Jena (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 32 days.

This patent is subject to a terminal disclaimer.

(21) Appl. No.: 16/056,295

(22) Filed: Aug. 6, 2018

(65) Prior Publication Data

US 2018/0341826 A1 Nov. 29, 2018

Related U.S. Application Data

(63) Continuation of application No. 15/113,213, filed as application No. PCT/EP2015/051230 on Jan. 22, 2015, now Pat. No. 10,043,093.

(30) Foreign Application Priority Data

Jan. 24, 2014 (EP) .................................... 14152477

(51) Int. Cl.
*G06K 9/00* (2006.01)
*G06K 9/34* (2006.01)
(Continued)

(52) U.S. Cl.
CPC .............. *G06K 9/344* (2013.01); *A61M 5/24* (2013.01); *A61M 5/3155* (2013.01);
(Continued)

(58) Field of Classification Search
CPC ...... G06K 9/344; G06K 9/2054; G06K 9/228; G06K 9/4604; G06K 9/4642;
(Continued)

(56) References Cited

U.S. PATENT DOCUMENTS 4,377,803 A * 3/1983 Lotspiech ................ G06K 9/34
382/171
5,034,991 A 7/1991 Hagimae et al.
(Continued)

FOREIGN PATENT DOCUMENTS

JP H7-325880 12/1995
JP H8-334377 12/1996
(Continued)

OTHER PUBLICATIONS

Casey et al., "A Survey of methods and strategies in character segmentation", Ieee Transactions on Pattern Analysis and Machine Intelligence, Jul. 1, 1996, 18(7).
(Continued)

*Primary Examiner* — Jose L Couso
(74) *Attorney, Agent, or Firm* — Fish & Richardson P.C.

(57) ABSTRACT

A supplemental device for attachment to an injection device, the supplemental device comprising:
an imaging arrangement configured to capture an image of one or more numbers present on a moveable component of the injection device; and
a processor arrangement configured to run a first algorithm to:
receive data representing an image;
(Continued)

determine the position of at least one number in the image by determining the boundaries of each visible number;

select one of the visible numbers to be identified;

perform a pattern matching process to identify the value of the selected number; and determine a dose dialled into the injection device using the determined position of the selected one of the at least one visible number in the image.

20 Claims, 7 Drawing Sheets

(51) Int. Cl.
    *A61M 5/24*     (2006.01)
    *A61M 5/315*     (2006.01)
    *G06K 9/46*     (2006.01)
    *G06K 9/20*     (2006.01)
    *G06K 9/22*     (2006.01)
    *G06K 9/62*     (2006.01)
    *A61M 5/31*     (2006.01)

(52) U.S. Cl.
    CPC ....... *A61M 5/31525* (2013.01); *G06K 9/2054* (2013.01); *G06K 9/228* (2013.01); *G06K 9/4604* (2013.01); *G06K 9/4642* (2013.01); *G06K 9/4647* (2013.01); *G06K 9/4661* (2013.01); *G06K 9/6202* (2013.01); *A61M 2005/3126* (2013.01); *A61M 2205/3306* (2013.01); *A61M 2205/52* (2013.01); *A61M 2205/8206* (2013.01); *G06K 2209/01* (2013.01); *G06K 2209/03* (2013.01)

(58) Field of Classification Search
    CPC .. G06K 9/4647; G06K 9/4661; G06K 9/6202; G06K 9/3283; G06K 9/348; G06K 9/3275; G06K 9/46; G06K 9/48; G06K 9/6217; G06K 9/68; G06K 9/38; G06K 9/20; G06K 9/32; G06K 9/34; G06K 2209/01; G06K 2209/03; G06K 2209/15; A61M 5/24; A61M 5/14; A61M 5/178; A61M 5/20; A61M 5/31; A61M 5/315; A61M 5/31525; A61M 5/31555; A61M 5/31533; A61M 5/31546; A61M 5/31553; A61M 5/31551; A61M 5/31556; A61M 5/31558; A61M 5/31566; A61M 5/31573; A61M 2205/3306; A61M 2205/8206; A61M 2205/50; A61M 2205/52; A61M 2205/502; A61M 2205/583; A61M 2205/6063; A61M 2205/6072; A61M 2205/6081; A61M 2205/3317; G06F 3/0482; G06F 19/3468; G06F 19/3418; A61B 5/4839; G01F 11/00; G01F 11/025; G01F 15/06; G01F 15/061; G01F 15/068; G01F 11/027; G01F 11/029; G09F 9/00
    See application file for complete search history.

(56) References Cited

U.S. PATENT DOCUMENTS

| | | | |
|---|---|---|---|
| 5,243,668 | A | 9/1993 | Kitamura et al. |
| 6,473,517 | B1* | 10/2002 | Tyan ...................... G06K 9/344 |
| | | | 382/105 |
| 8,873,856 | B1 | 10/2014 | Chapleau |
| 9,067,022 | B2* | 6/2015 | Baek ...................... A61M 5/178 |
| 9,125,991 | B2 | 9/2015 | Schabbach |
| 9,526,842 | B2 | 12/2016 | Oh |
| 9,623,188 | B2 | 4/2017 | Nielsen |
| 2008/0310721 | A1* | 12/2008 | Yang ................... G06K 9/3275 |
| | | | 382/182 |
| 2010/0286612 | A1 | 11/2010 | Cirillo |
| 2012/0053527 | A1 | 3/2012 | Cirillo et al. |
| 2013/0245545 | A1 | 9/2013 | Arnold |
| 2013/0336555 | A1 | 12/2013 | Baek et al. |
| 2015/0306304 | A1 | 10/2015 | Schabbach |
| 2017/0138769 | A1 | 5/2017 | Jones |
| 2017/0154232 | A1 | 6/2017 | Hamen |
| 2017/0182258 | A1 | 6/2017 | Michael |

FOREIGN PATENT DOCUMENTS

| | | |
|---|---|---|
| JP | H10-288504 | 6/2010 |
| JP | 2010-123090 | 6/2016 |
| WO | WO 2011/117212 | 9/2011 |
| WO | WO 2013/120776 | 8/2013 |

OTHER PUBLICATIONS

Elliman et al., "A review of segmentation and contextual analysis techniques for text recognition", Pattern Recognition, Elsevier, GB, Jan. 1, 1990, 23(3/04):337-346.

Gupta et al., "OCR binarization and image pre-processing for searching historical documents", Pattern Recognition, Elsevier, GB, Oct. 29, 2006, 40(2):89-397.

International Preliminary Report on Patentability in International Application No. PCT/EP2015/051230, dated Jul. 26, 2016, 9 pages.

International Search Report and Written Opinion in International Application No. PCT/EP2015/051230, dated Apr. 24, 2015, 15 pages.

Liang et al., "Efficient algorithms for segmentation and recognition of printed characters in document processing", Communications, Computers, and Signal Processing, May 19, 1993, pp. 240-243.

Liang et al., "Segmentation of touching characters in printed document recognition", Document analysis and recognition, Oct. 20, 1993, pp. 569-572.

Lu Y, "Machine printed character segmentation—an overview", Pattern Recognition, Elsevier, GB, vol. 28, No. 1, Jan. 1, 1995, pp. 67-80.

Jung et al., "Machine printed character segmentation method using side profiles", Systems, Oct. 12, 1999, 6:863-867.

Oivind et al., "Feature extraction methods for character recognition—A Survey", Pattern Recognition, Elsevier, GB, Apr. 1, 1996, 29(4):641-661.

Sunghoo et al., "Localizing slab identification numbers in factory scene images", Expert Systems Applications, Jan. 12, 2012, 39(9).

Wei et al., "An automated vision system for container-code recognition", Expert Systems with Applications, Aug. 14, 2011, 39(3):2842-2855.

Xiaodan et al., "A Novel Algorithm for Character Segmentation of Degraded License Plate Based Prior Knowledge", Automation and Logistics, Aug. 1, 2007, pp. 249-253.

\* cited by examiner

SUPPLEMENTAL DEVICE FOR ATTACHMENT TO AN INJECTION DEVICE FOR RECORDING AND DISPLAYING A DOSE VALUE SET BY THE USER USING OPTICAL CHARACTER RECOGNITION (OCR)

CROSS-REFERENCE TO RELATED APPLICATIONS

This application is a continuation of U.S. application Ser. No. 15/113,213, filed on Jul. 21, 2016, which is a U.S. national stage application under 35 USC § 371 of International Application No. PCT/EP2015/051230, filed on Jan. 22, 2015, which claims priority to European Patent Application No. 14152477.7, filed on Jan. 24, 2014 The entire contents of each of these applications are incorporated herein by reference.

TECHNICAL FIELD

The present invention relates to a supplemental device for attachment to an injection device, wherein the supplemental device comprises an imaging arrangement and a processor arrangement configured to detect one or more spaces which separate successive numbers present on the injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

A first aspect of the invention provides a supplemental device for attachment to an injection device, the supplemental device comprising:
an imaging arrangement configured to capture an image of one or more numbers present on a moveable component of the injection device; and
a processor arrangement configured to run a first algorithm to:
receive data representing an image;
determine the position of at least one number in the image by determining the boundaries of each visible number;
select one of the visible numbers to be identified;
perform a pattern matching process to identify the value of the selected number; and
determine a dose dialled into the injection device using the determined position of the selected one of the at least one visible number in the image.

Using the determined position of the selected one of the at least one visible number to determine a dose dialled into the injection device may comprise calculating a position offset of the selected number from the centre of the image and applying a weighting function based on the position offset to the value of the selected number. The processor may also perform a binarization process on the received image data.

One or more of the numbers in the image may only be partially visible.

Determining the boundaries of each visible number may comprise recording the sum of black pixels in each pixel row of the image and identifying one or more rows in which the sum is below a threshold value. Determining the boundaries of each visible number may further comprise recording the sum of black pixels in each pixel column of the image and identifying one or more columns in which the sum is below a threshold value. The threshold value may be 1.

Performing the pattern matching process may comprise:
if the selected number comprises two or more digits, separating the digits; and
comparing the digit or digits to stored digit templates to determine a best match.

Selecting one of the visible numbers to be identified may comprise selecting the number having the greatest height, or if two numbers are of equal height, the uppermost of the numbers.

The processor may be pre-programmed with values for the expected height and width of the numbers visible in the image.

The processor arrangement may be further configured to cause a value corresponding to a result of the application of the weighting function to the value of the selected number to be displayed on a display of the device.

The processor arrangement may be further configured to run a second algorithm on the received data representing an image, wherein the second algorithm differs in at least one step from the first algorithm. The processor arrangement may be further configured to compare a result of the first algorithm and a result of the second algorithm in order to determine a dose dialled into the injection device.

A second aspect of the invention provides a system comprising the supplemental device of the first aspect of the invention and an injection device having a moveable component with numbers present thereon.

A third aspect of the invention provides a method of determining a dose dialled into an injection device using a supplemental device for attachment to an injection device, comprising:
an imaging arrangement of the supplemental device capturing an image of one or more numbers present on a moveable component of the injection device;
a processor arrangement of the supplemental device:
receiving data representing an image;
determining the position of at least one number in the image by determining the boundaries of each visible number;
selecting one of the visible numbers to be identified;
performing a pattern matching process to identify the value of the selected number; and determining a dose dialled into the injection device using the determined position of the selected one of the at least one visible number in the image.

Using the determined position of the selected one of the at least one visible number to determine a dose dialled into the injection device may comprise calculating a position offset of the selected number from centre of the image and applying a weighting function based on the position offset to the value of the selected number.

BRIEF DESCRIPTION OF THE FIGURES

The figures show:

FIG. 1b shows a perspective view of some detail of the drug delivery device of FIG. 1a;

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1A:
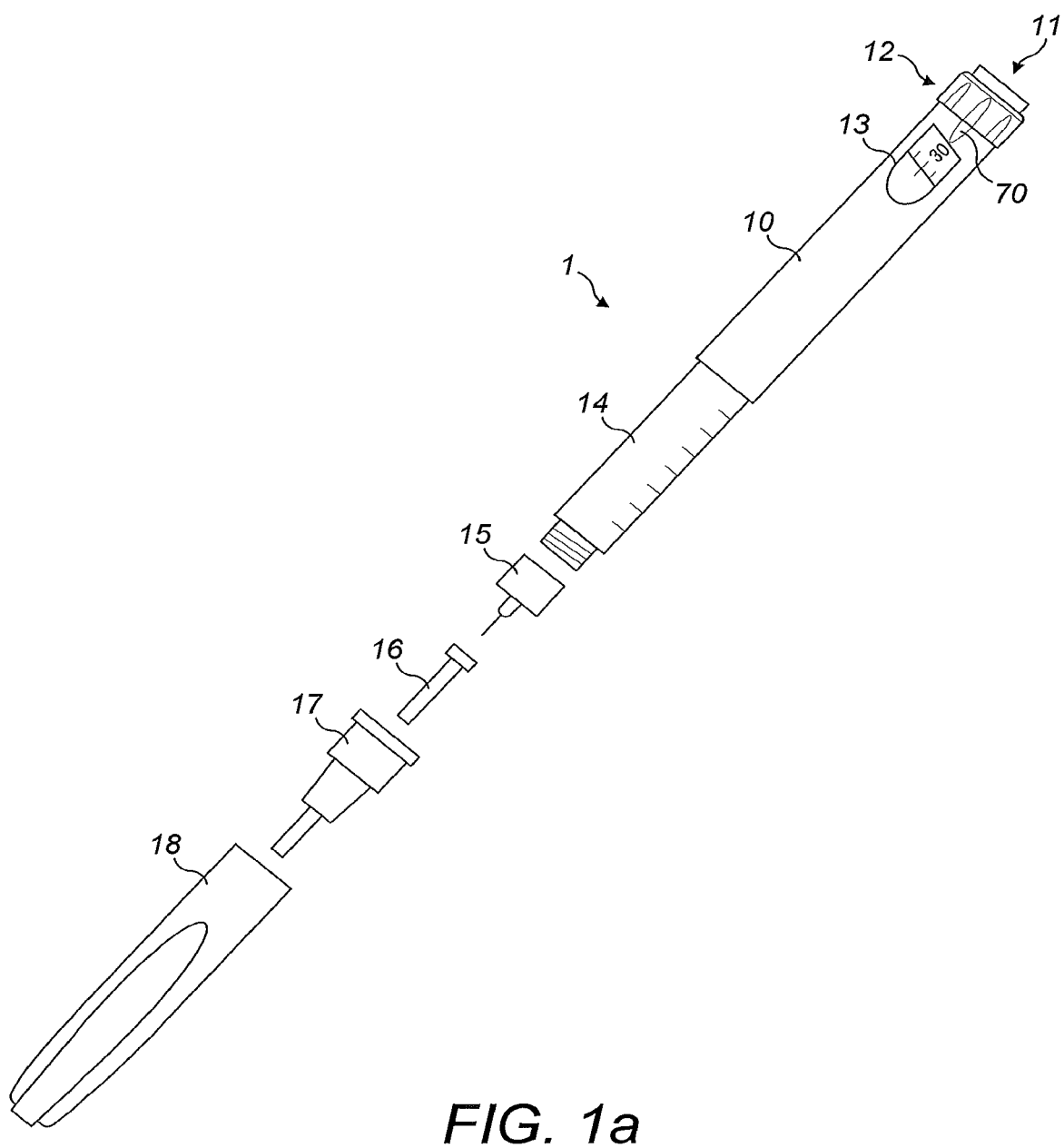
FIG. 1a: an exploded view of an drug delivery device.

FIG. 1a is an exploded view of an injection device 1, which may for instance represent Sanofi's Solostar® insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a colour. The information identifying the medicament may also be encoded into a barcode, QR code or the like. The information identifying the medicament may also be in the form of a black and white pattern, a colour pattern or shading.

Turning the dosage knob 12 causes a mechanical click sound to provide acoustical feedback to a user. The numbers displayed in dosage window 13 are present on a sleeve by printing and the sleeve is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body.

Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
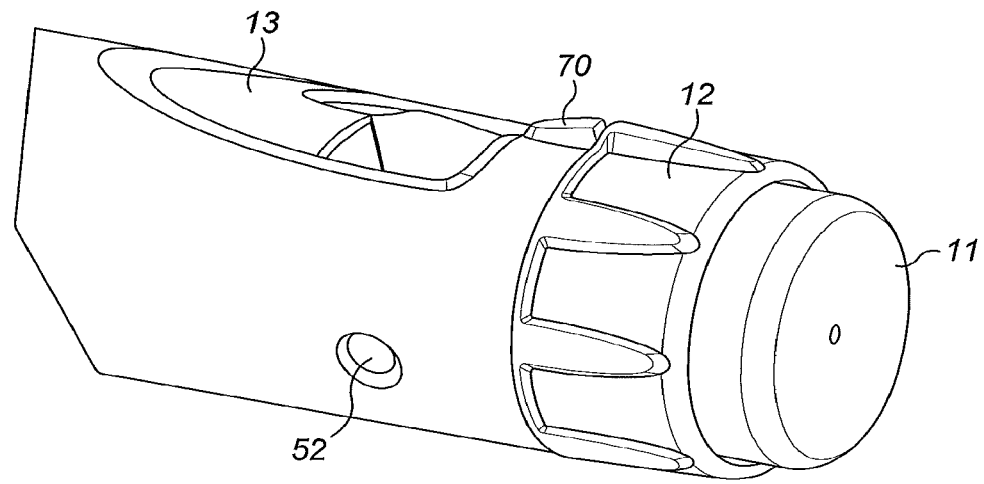

FIG. 1b is a close-up of the end of the injection device 1. This FIG. shows a locating rib 70 that is located between the viewing window 13 and the dosage knob 12.

Figure 2A:
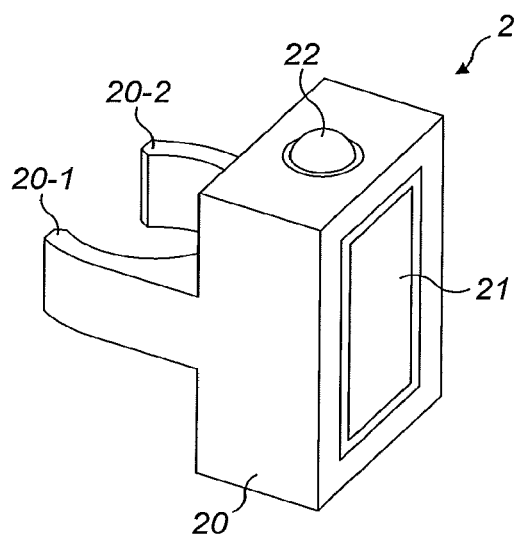
FIG. 2a: a schematic illustration of a sensor device to be releasably attached to the drug delivery device of FIGS. 1a and 1b according to an aspect of the present invention.

FIG. 2a is a schematic illustration of an embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
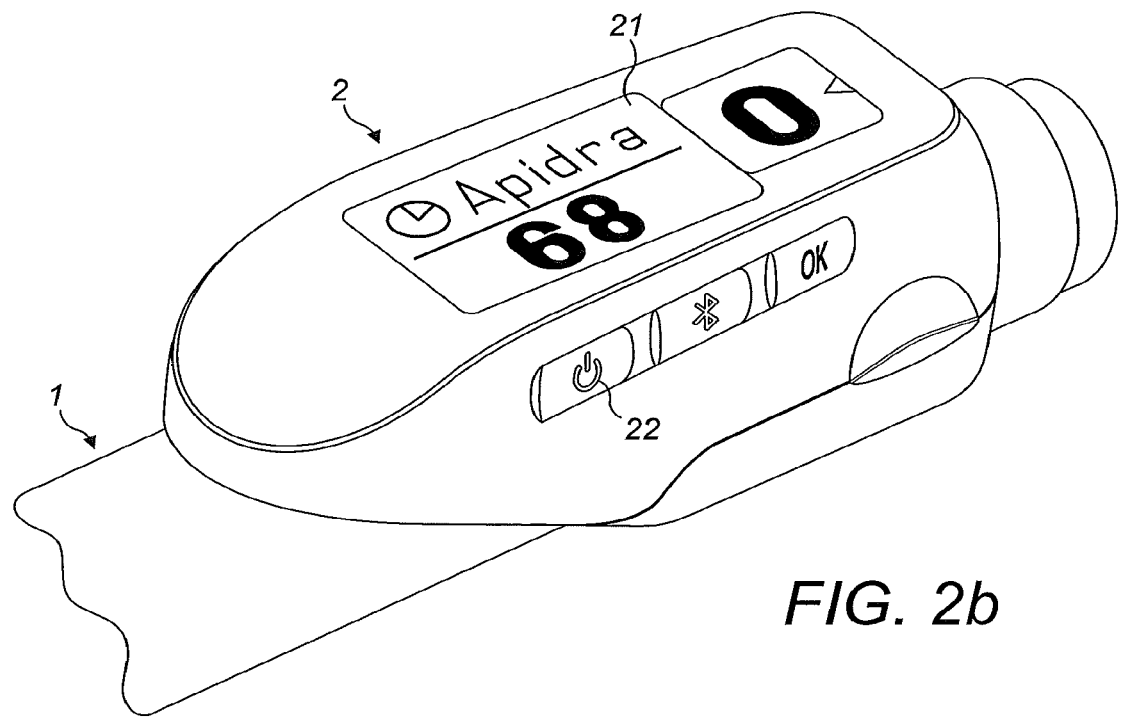
FIG. 2b: a perspective view of a sensor device to be releasably attached to the drug delivery device of FIGS. 1a and 1b according to various aspects of the present invention.

FIG. 2*b* is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
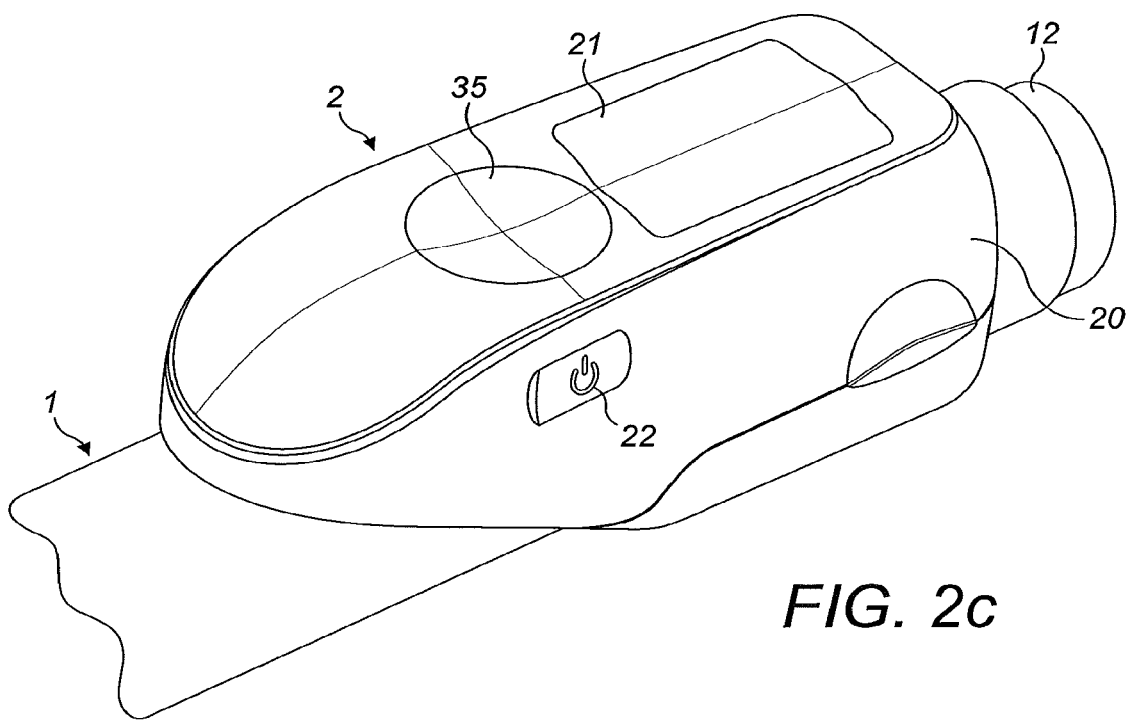
FIG. 2c: a perspective view of a sensor device to be releasably attached to the drug delivery device of FIGS. 1a and 1b according to other aspects of the present invention.

FIG. 2*c* is a schematic illustration of a third embodiment of a supplementary device 2 to be releasably attached to injection device 1 of FIG. 1*a*. Supplementary device 2 comprises a housing 20 with a mating unit configured to embrace the housing 10 of injection device 1 of FIG. 1*a*, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
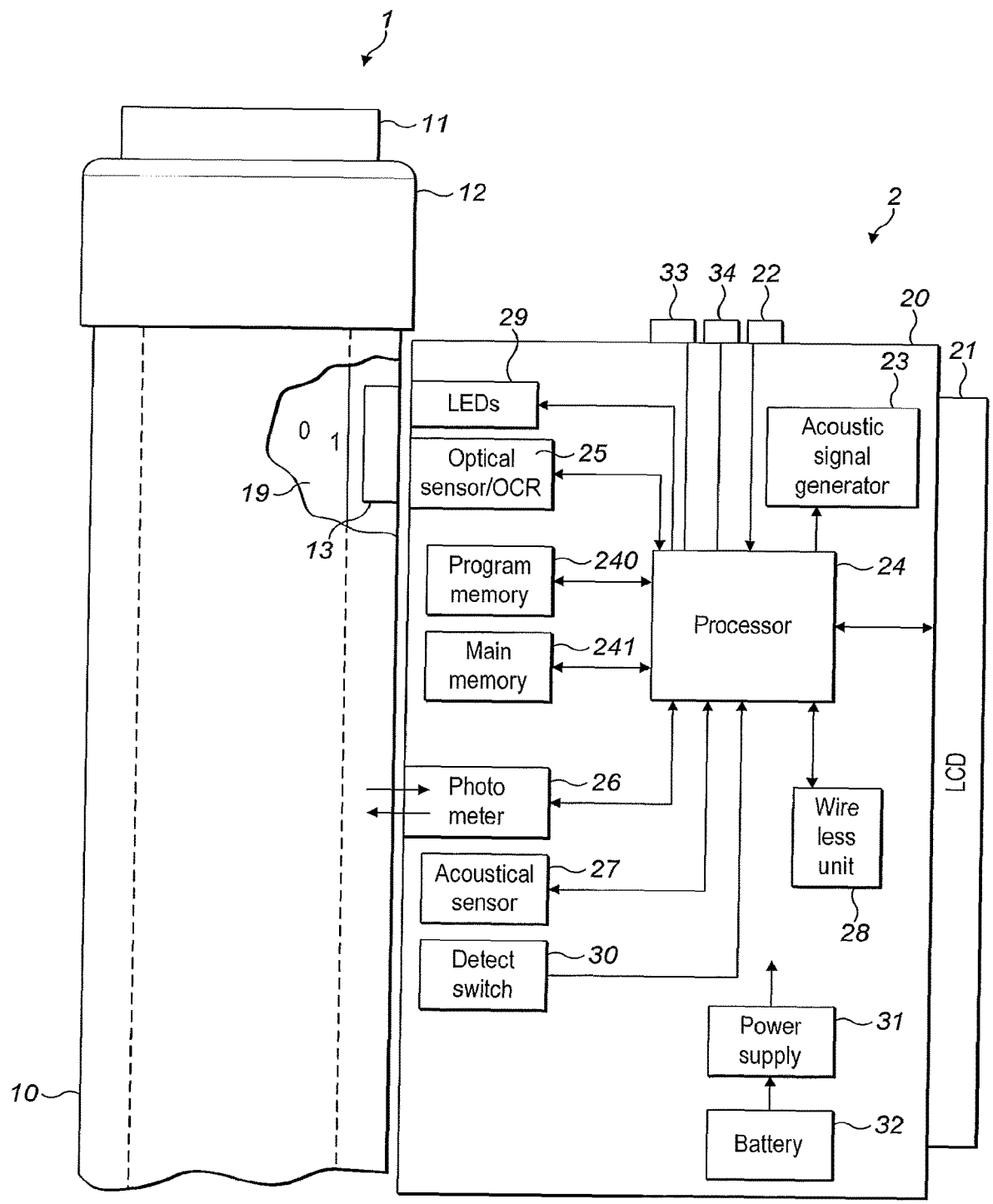
FIG. 3: a schematic view of a sensor device attached to a drug delivery device showing components of the sensor device.

FIG. 3 shows a schematic view of the supplementary device 2 of FIG. 2*a* in a state where it is attached to injection device 1 of FIG. 1*a*.

With the housing 20 of supplementary device 2, a plurality of components are contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2*b*, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2*c*, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers, characters, symbols or glyphs present on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ration may be 0.15.

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a oneor two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 4:
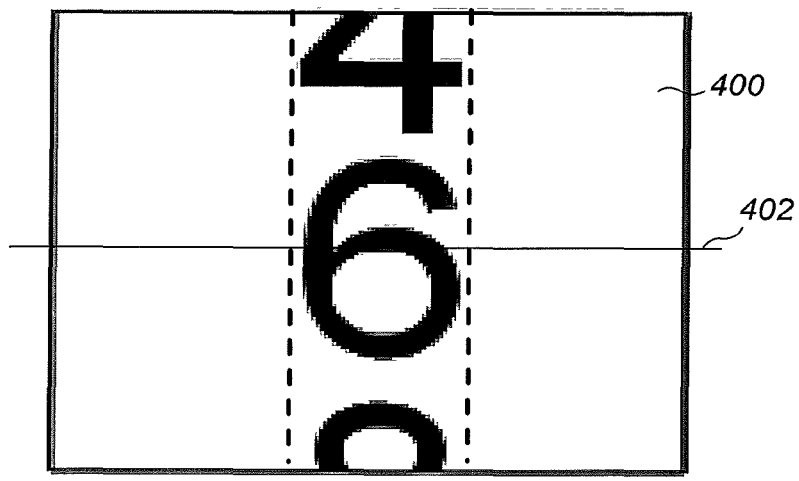
FIGS. 4 and 5 show diagrammatically examples of the field of view of an optical sensor relative to a dose window.
Figure 5:
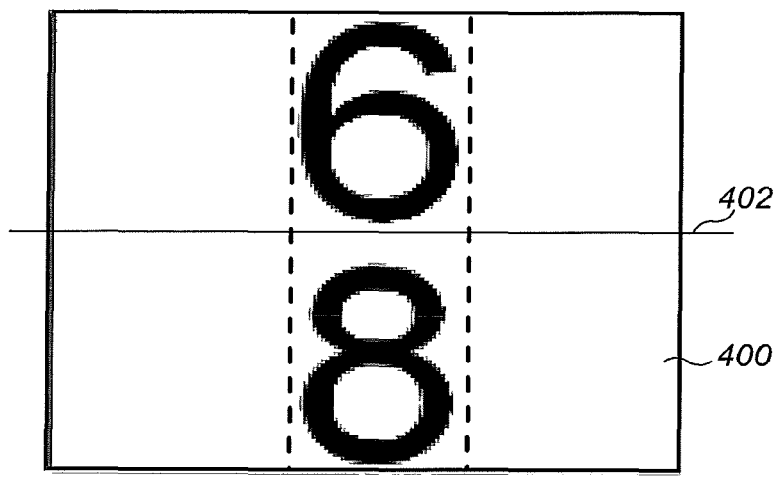

FIGS. 4 and 5 show schematically examples of the field of view 400 of the optical sensor 25 when the supplemental device 2 is attached to the injection device 1. The field of view of the sensor may be rectangular or square. The field of view 400 of the optical sensor may be wider than the dose window 13, but not as tall and therefore does not take in the whole of the dose window 13. However, in some other embodiments, the field of view may be larger than the dose window 13 in both directions. The solid horizontal line 402 in FIGS. 4 and 5 represents the centre line of the field of view 400 (i.e. the central pixel row of the optical sensor's 25 pixel array).

In some embodiments, due to space restrictions and the need for the numbers to be of a certain size, only even numbers are printed on the number sleeve 19. In some other embodiments, only odd numbers may be printed on the number sleeve. However, any number of units of medicament can be dialled into the injection device 1. In some alternative embodiments, every number, i.e. ascending integer numbers, may be printed on the sleeve. In these embodiments, it may be possible to dial half-unit doses into the injection device. The injection device may be limited to a maximum dialled dose of 80 units. In further alternative embodiments, only every $3^{rd}$, $4^{th}$ or $5^{th}$ number may be printed. The dose positions between the printed numbers may be indicated by tick marks. The term "printed" is used herein to indicate that the numbers are marked on the surface of the number sleeve, however the skilled person would understand that the numbers may be printed, etched, marked, attached, or otherwise made visible to the optical sensor 25 of the supplementary device 2 in a number of known ways.

The injection device 1 and supplemental device 2 are configured such that the field of view 400 of the optical sensor 25 is positioned approximately centrally over the dose window 13. Manufacturing tolerances may mean that the field of view is off-centred slightly, both in the horizontal and vertical directions. In FIG. 4, 6 units are dialled into the injection device 1 such that the number 6 is displayed centrally in the dose window 13. In FIG. 5, 7 units are dialled into the injection device 1 such that the numbers 6 and 8 are both displayed in the dose window 13 and the space between these numbers occupies the central region of the dose window 13.

The processor 24 is configured to execute an algorithm which allows both of the situations represented by FIGS. 4 and 5 to be decoded accurately. This algorithm performs an optical character recognition (OCR) process on the visible numbers and uses the results of the OCR process in order to determine accurately the dose which is currently dialled into the injection device 1. The algorithm may be embodied in software or firmware and may be stored in the program memory 240 of the supplemental device 2. The processor 24 and memory 240 storing the algorithm together may be referred to herein as a "processor arrangement".

The entire algorithm can be divided into a pre-processing part, an OCR-part, and a post-processing part, wherein each part generally involving several steps.

In the pre-processing part image data quality is assessed and improved by executing the following steps:
 Defective and bad pixel correction
 Light correction
 Distortion and slant correction For example, an exposure control algorithm rejects pictures that are too bright or too dark and a new picture is taken with adjusted exposure parameters. The numbers may be printed on a slant for ease of recognition and positioning by a human, but may be easier to decode if this slant is removed. For the purpose of the invention described and claimed herein, the pre-processing is an optional feature. The OCR part of the algorithm can be designed to perform to the required standard without pre-processing of the image and/or the optical sensor 25 can be configured to produce images of sufficient quality for OCR to be performed on them directly.

In the OCR part, the image data is then further processed and at the end a recognized character is available. The OCR process comprises the steps of:
Binarization
Segmentation
Pattern matching
Position calculation These steps are described in greater detail below.

The post-processing may involve various checks and the production of a result to be displayed. The post-processing comprises the following steps:
Perform sanity checks
Hysteresis calculation
Show end result on display For the purpose of the invention described and claimed herein, the post-processing is an optional feature. For example the result of the OCR process may be output directly to a display device without post-processing.

Due to the high reliability requirements of the sensor device 2, there may in some embodiments be two OCR algorithms that are operated in parallel. The two OCR algorithms have the same input (image) and are intended to provide the same output. They both perform similar steps however the individual methods used in each step may vary. These two OCR algorithms may differ in one of the binarization, segmentation, pattern matching and position calculation steps or in more than one of these steps. Having two OCR-parts which use different methods to provide the same result increases the reliability of the entire algorithm as the data has been processed in two independent ways.

A key challenge is to implement an image capture and subsequent OCR process including segmentation into a small system that is reliably capable of recognizing numbers, characters, and/or glyphs from a display to determine a dose value. The system is battery powered, small and has limited imaging as well as processing capabilities owed to the compact design and life time requirements. A processor for this kind of device typically has a clock rate of about 100 MHz or below, a memory of up to 32 kByte RAM and 512 kb flash (these specifications are exemplary and not intended to be limiting). However, the result of the OCR process should be available in real time, meaning that the user dialling in a dose can read it from the supplemental device while dialling. A typical computation time would be about 70 ms.

Figure 6:
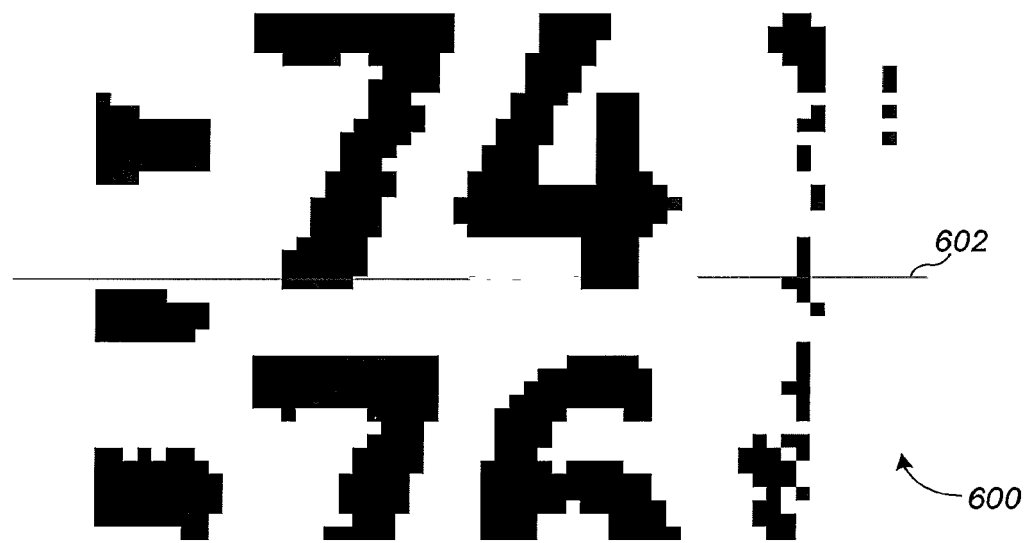
FIG. 6 shows an example of a binarized image of the dose window.

The OCR part of the algorithm will now be described in greater detail. FIG. 6 shows an example of an image 600 of the dose window 13 after binarization. The solid horizontal line 602 represents the centre line of the field of view of the optical sensor 25. An image of the dose window 13 is first captured by the optical sensor 25. After applying the pre-processing steps described above, a greyscale image is converted into a purely black and white image through a binarization process. According to a design of injection pen having dark numbers on a bright sleeve, the black and white image would indicate the presence of digits with black pixels and the absence of digits with white pixels.

In some embodiments a fixed threshold is used to separate between black and white pixels. Pixels that have a value at or above the threshold become white, pixels below the threshold become black in the binarized picture. A high threshold will lead to artefacts (black parts in white areas), whereas a low threshold has the risk that in some cases parts of digits are missing. In some embodiments, the threshold is chosen so that in no case are parts of digits are missing because the algorithm is in general robust against artefacts (i.e. an accurate OCR process can be performed in the presence of some artefacts). In tests, a sensor capable of detecting 256 grey values was used and a threshold value of 127 showed good results.

The use of a fixed threshold is possible because of the light correction in the pre-processing. The combination of the light correction and the fixed threshold is similar to a windowed mean binarization. A windowed mean binarization compares the pixel-value with the mean value of the pixels of the area where it is located. Performing the light correction step before the distortion and slant correction steps means that more information is available to be used for the OCR process, which has been shown to yield better results on the edges and corners of the picture.

Alternatively, the Otsu threshold method may be applied to the captured greyscale image to produce a binary image similar to image 600. In some alternative embodiments, the binarization may be omitted and the OCR part of the algorithm may be performed on the captured greyscale image.

After binarization, the segmentation step is performed. The goal of this part of the algorithm is to determine the exact location of each visible or partly visible number in the image. To achieve this, the algorithm defines the boundaries of the visible digits by finding the edges of the digits. This is generally accomplished in two steps, which may be performed in any order. Referring again to FIGS. 4 and 5, the processor 24 first performs a "vertical projection" in which the pixel columns making up the binarized image are analysed. Each pixel column is analysed individually and the sum of the number of black pixels in each column is computed. In some embodiments, only a pixel column having zero black pixels may define the edge of a number. Alternatively, a low threshold for the number of black pixels may be set to account for dirt, scratches and other disturbances. Difference values for adjacent columns are calculated and the boundary having the greatest difference represents the edge of the number. Additionally, the pixel content of overlapping groups of columns (e.g. three adjacent columns) may be calculated to aid in determining the horizontal edges of the numbers.

The dashed lines visible in FIGS. 4 and 5 illustrate the expected result of the "vertical projection".

Figure 7:
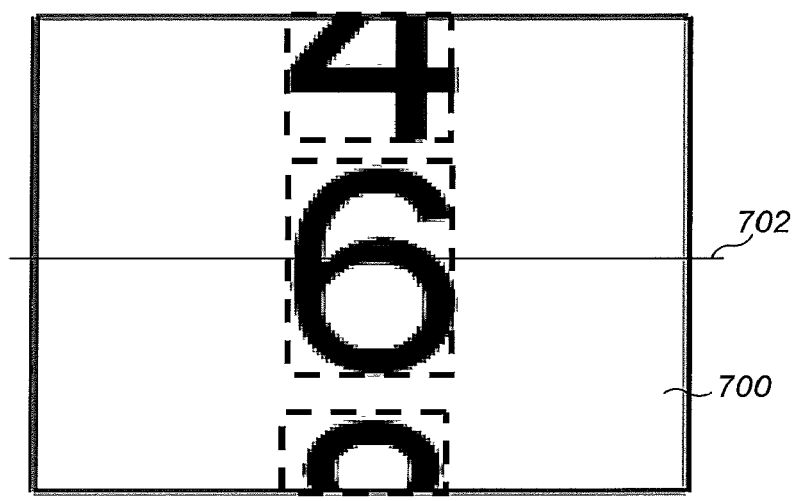
FIGS. 7 and 8 show diagrammatically further examples of the field of view of the optical sensor and the expected result of a segmentation process.
Figure 8:
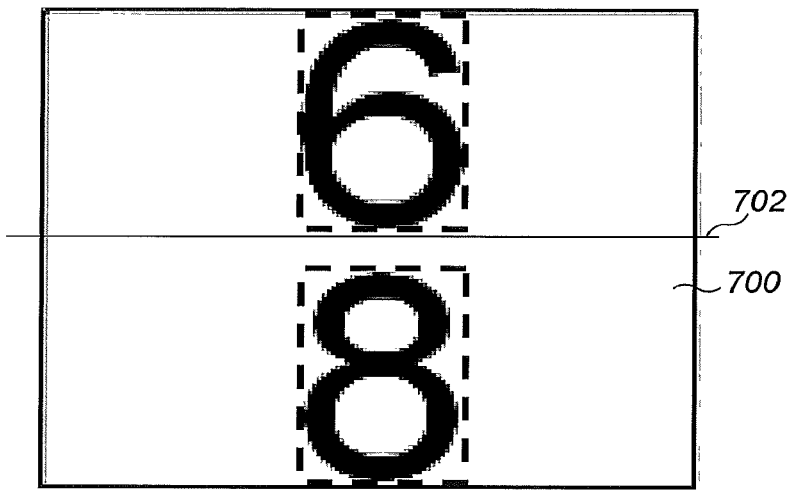

The processor 24 then performs a "horizontal projection" in which the pixel rows making up the binarized image are analysed. This proceeds in the same way as described above for the vertical projection. Referring now to FIGS. 7 and 8, the field of view 700 of the optical sensor 25 is again shown. The solid horizontal line 702 represents the centre line of the field of view of the optical sensor 25. The expected result of the horizontal projection is added to that of the vertical projection such that the edges of the visible numbers are identified. The dashed lines illustrate the expected result of this process. In FIG. 8, the numbers "6" and "8" are both fully visible and the segmentation process therefore detects all four edges (left, right, top and bottom) of both of these numbers. This would correspond to a user having dialled 7 units. In FIG. 7, the number "6" is centrally located in the filed of view 700 and the numbers "4" and "8" are partially visible above and below. This would correspond to a user having dialled 6 units. Thus, not all of the edges of the partially visible numbers are detected. The processor 24 may be pre-programmed with the expected height (in pixel rows) of a full number, and so is able to recognise the presence of partially visible numbers.

It is straightforward to see that the "horizontal projection" and the "vertical projection" could equally well be based on an analysis where the sum of white pixels is computed instead, provided that the expected number of white pixels in each row and column is known.

Knowing the exact location allows for using only the part of the image which represents the visible number or numbers for the next steps in the OCR process. By this any impact of other objects besides the number, e.g. dirt, scratches and other disturbances, can be reduced. Further, the total number of pixels to be processed in subsequent steps, e.g. in the pattern matching step, is also reduced. This helps reducing resource requirements. This also helps increasing performance. In addition, knowing the exact location also supports determining the vertical position relative to the centre of the image (see below).

The next step in the OCR process is to select one of the visible numbers to be decoded and identified. This is done by designating one of the numbers as the "primary digit row". The primary digit row is selected based on which visible number has the greatest height. This is because all of the numbers printed on the sleeve have approximately the same height and it can be assumed that the number having the greatest height will be fully visible and therefore easy to decode with a high degree of certainty. In FIG. 7, the number "6" has a greater height than the partially visible numbers above and below and is selected as the primary digit row. In FIG. 8, both the numbers "6" and "8" are fully visible and have the same height. In this case, the uppermost number is selected as the primary digit row. The primary digit row is the number which is subsequently used to determine the dose dialled into the injection device 1.

Figure 9:
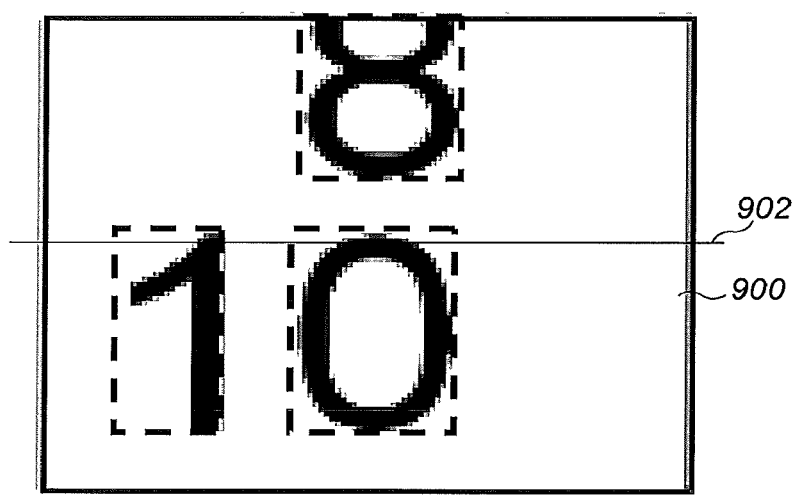
FIG. 9 shows a further example of the field of the field of view of the optical sensor in the case where the primary digit row contains two digits.

A standard injection device 1 for self administration of insulin can inject any number of units of medicament from 1 to 80 units. Therefore, in order to properly decode the number identified as the primary digit row, it must be determined whether the number consists of one or two digits. The processor 24 therefore performs a series of steps in order to determine whether each number consists of one or two digits, and in the latter case, to separate the digits from each other. The processor 24 may use the column pixel information previously calculated for this purpose. Referring now to FIG. 9, another exemplary field of view 900 is shown in which 9 units of medicament are dialled into the injection device 1. The expected results of the horizontal and vertical projections are shown. The number "10" is of greater height than the number "8" and is selected as the primary digit row.

After this the processor 24 determines whether the selected primary digit row is wider than a pre-defined "maximum digit width" value. As the processor 24 is pre-programmed with information relating to the expected size of the numbers in the captured images, a maximum expected width for a single digit can be defined. In order to increase reliability, the maximum width may be set as a small number of pixel columns more than the widest number. If the width of the primary digit row is the maximum digit width or less, it is assumed that the row contains a single digit. If the primary digit row is too wide to be a single digit, then a second vertical projection is then performed on the primary digit row (rather than on the whole image). In addition, the expected width of each individual digit may be used to predict the point at which the separation should occur.

The exemplary field of view 900 shown in FIG. 9 is a diagrammatic representation in which the numbers are well spaced. In reality, the numbers may be printed quite close together owing to the limited space available of the number sleeve and the need for the numbers to be readable to a user when the supplemental device 2 is not being employed. Thus, after binarization, the two digits making up the number may not be cleanly separated, i.e. there may not be a column having no black pixels between the two digits. This is the case in the exemplary binarized image shown in FIG. 6, in which the "7" and "4" of the upper number "74" do not have a pixel column between them containing no black pixels. In this case, the expected width of each individual digit is again used to predict the point at which the separation should occur. If the predicted column contains black pixels, then the deviations of this column from adjacent columns are calculated to determine the best separation point. In this situation, as it is not clear whether the black pixels in the chosen separating column belong to the left or right digit, they are ignored. This has been shown to have a minimal effect on the reliability of the OCR process to correctly identify the digits.

A pattern matching process is then performed to identify the digits in the primary digit row. Templates for each number may be stored in a memory of the supplementary device 2 and the identified digits may then be compared to these templates. In a straight forward approach the pattern matching could be performed on a pixel-by-pixel basis. However, this may require high computing power. Furthermore, this approach is prone to position variation between the image and the template. In some other embodiments, a feature recognition process is performed. Features may be horizontal, vertical or diagonal lines, curves, circles or closed loops etc. Such features may be recognized in the image of the selected number and compared with templates.

In yet further embodiments, the pattern matching algorithm may be based on a vector comparison process. For example, the templates may be in the form of vectors describing the position and length of each line (continuous run) of black pixels. In one example, the position and length relate to the absolute position in the respective line. In another example, the position and length relate to a vertical line extending through the centre of the template. The captured binary image of each digit may similarly be converted into vectors and compared with each stored template in turn to find the best match.

When comparing the vectors of the captured image with a particular digit template, any deviations result in a penalty being applied for the likelihood of a match between the image and that template. The magnitude of the penalty may depend on the number of missing or extra black pixels in the image compared to the template. After the digit image has been compared with each template and all of the penalties have been applied a decision is made as to which digit is present. In good optical conditions, the correct template will have a very low penalty, while all other templates will have a high penalty. If the primary digit row consists of two digits, this process is performed on both digits and the processor 24 then combined the outcomes to produce a final result for the number.

Special measures may exist for certain digits. For example, "1" deviates substantially in width from all other digits resulting in common misdetections. To counter this, if a binary image of a digit is wider than the expected width of "1", then it receives an additional detection penalty when being compared with the stored vector template of "1".

In some exceptional cases, if the confidence level in the result of the pattern matching of the primary digit row is below a certain threshold (e.g. 99%), then the processor may perform a second pattern matching process on one or more of the other visible or partially visible numbers. Since the order of the numbers is known, this second pattern matching can act as a check that the first pattern matching returned the correct result.

If the confidence level in the result is still not high enough, then a second image may be captured by the optical sensor 25 and the process repeated. Alternatively, an error message may be displayed.

Once the digit or digits of the primary digit row have been successfully identified, a weighting function is applied in order to determine a dose dialled into the injection device 1. To formulate the weighting function, the vertical position of the primary digit row relative to the centre of the image is determined. This may be done by calculating the offset of the middle pixel row comprising the primary digit row relative to the pixel row of the optical sensor 25 representing the centre line of the image.

For example, in some embodiments the optical sensor comprises a rectangular 64×48 array of photosensitive elements. The resulting binary image is a pixel array having these same dimensions. The $24^{th}$ and/or $25^{th}$ pixel row may be designated as the central row of the image. The position of the middle pixel row comprising the primary digit row is determined. The offset, in pixel rows, between the middle pixel row comprising the primary digit row and the central row or rows of the image is then calculated. This offset may be positive or negative depending on the direction of the offset. The offset is converted into a fraction by dividing it by the distance (in pixel rows) between successive numbers before being applied to the determined numbers accordingly. The offset therefore allows for determining the rotational position of the number relative to the sensor. If the central pixel row of the primary digit row is the same as the central pixel row of the image, then the offset is zero and the position is equal to the primary digit row number. However, due to manufacturing tolerances in the supplementary device 2, and or in the injection device 1 and due to pressure applied on the number sleeve by a user, there is likely to be some offset in most circumstances.

The distance between successive numbers printed on the number sleeve is constant, since the numbers represent a dose which is related to a discrete mechanical movement of the injection device mechanism. Therefore, the distance (in pixel rows) between successive numbers in the captured image should also be constant. The expected height of the numbers and spaces between the numbers is pre-programmed into the algorithm.

As an example, the expected height of each numbers may be 22 pixels and the expected height of the spaces between the numbers may be 6 pixels. Therefore, the distance between the central pixel rows of successive numbers would be 28 pixels.

Continuing this example, if the pixel rows are numbered sequentially from the top to the bottom of the image, the application of the weighting function may be defined mathematically as:

Position=primary digit row number+[2×offset/(expected height of number+expected height of space)]

Where offset=central image row number−primary digit row central row number

Thus, if the primary digit row is in the upper half of the image, then the offset is positive and if the primary digit row is in the lower half of the image, then the offset is negative.

For example, if the number shown in the primary digit row is "6", as in FIG. 4, and the offset is zero, then the calculated position would be:

Position=6+[2×0/(28)]=6

Thus a result of "6" would be returned as expected.

Taking the example of FIG. 6 in which 75 units are dialled into the injection device 1, if the top number, "74", is selected as the primary digit row and there is a positive offset of 11 pixel rows according to the equation above, and again assuming a combined number/space height of 28 pixels, the calculated position would be:

Position=74+[2×11/(28)]=74.79

This result is then rounded up to the nearest whole number, to give a position determination of "75" as expected.

After applying the final post-processing part the processor 24 causes this result to be displayed on the display unit 21 of supplementary device 2. As previously discussed, due to space constraints, not every number may be printed on the number sleeve. In some embodiments, only even numbers are printed on the number sleeve. The position determination step described above allows the supplemental device 2 to display dose values, even though these values may not appear on the number sleeve. Thus a clearer indication of a dialled dose is provided to a user of the supplemental device 2.

If a user is dialling in a dose slowly (i.e. rotating the dosage knob 12 slowly), then the position rounding described above may cause a flickering of the display between two numbers. In order to prevent this, the post-processing step may contain hysteresis rules, such that the displayed number has some dependence on the previously displayed number. This hysteresis calculation may be the last step performed in the algorithm before the result is displayed.

The skilled person will appreciate that the above described weighting function and position determination represents only one example and that numerous other calculation methods may be used to arrive at the same result. The skilled person would also appreciate that the above described mathematical calculation may be modified and improved to reduce the computation time. Thus the exact form of the weighting function is not essential to a definition of the present invention.

In some embodiments, only every $3^{rd}$, $4^{th}$ or $5^{th}$ number may be printed on the sleeve, for example the sequence of numbers may be 0, 5, 10, 15 etc. The intermediate dose values may be indicated only by tick marks on the sleeve. In this case, the resolution of the optical sensor 25 is sufficient to allow the algorithm to determine an exact position of the number sleeve 19 and derive a dose unit value that is not imprinted by determining the positions of the visible numbers relative to the centre line of the sensor. For example, 7 units may be dialled into the injection device, such that the dose sleeve is rotated into a position between the printed numbers 5 and 10. In this case the position determination aspect of the algorithm is accurate enough to calculate a dose value of "7" using a modified form of the weighting function (as the height of the numbers and size of the space between the numbers may also be modified).

The algorithm may also be configured to perform other types of manipulation on the images numbers, for example by changing the size of one or more digits, cropping the numbers to a defined pixel area and shearing numbers printed in a italic font into an upright position. These manipulations may be performed before a pattern matching comparison with the stored templates. Alternatively, these manipulations may be performed in an image pre processing step on the captured images before the binarization process. Additional shading, distortion and exposure correction may also be performed.

The invention claimed is:

1. A supplemental device for attachment to an injection device, the supplemental device comprising:
   an imaging sensor configured to capture an image of one or more numbers displayed on a moveable component of the injection device;
   one or more processors; and
   a computer-readable memory storing instructions executable by the one or more processors to:
      receive data representing an image;
      determine a position of at least one number in the image by determining one or more boundaries of each visible number;
      select one of the visible numbers to be identified, wherein selecting one of the visible numbers to be identified comprises selecting the number having a greatest height;
      perform a pattern matching process to identify a value of the selected number; and
      determine a dose dialed into the injection device using the determined position of the at least one number in the image.

2. The supplemental device according to claim 1, wherein one or more of the numbers in the image is only partially visible.

3. The supplemental device according to claim 1, wherein the computer-readable memory stores instructions executable by the one or more processors to perform a binarization process on the received data.

4. The supplemental device according to claim 1, wherein determining the one or more boundaries of each visible number comprises recording a sum of black pixels in each pixel row of the image and identifying one or more rows in which the sum of black pixels is below a threshold value.

5. The supplemental device according to claim 1, wherein determining the one or more boundaries of each visible number comprises recording a sum of black pixels in each pixel column of the image and identifying one or more columns in which the sum of black pixels is below a threshold value.

6. The supplemental device according to claim 5, wherein the threshold value is 1.

7. The supplemental device according to claim 1, wherein performing the pattern matching process comprises:
   determining that the selected one of the visible numbers comprises two or more digits;
   in response to determining that the selected one of the visible numbers comprises two or more digits, separating the two or more digits; and
   comparing each digit to stored digit templates to determine a best match.

8. The supplemental device according to claim 7, wherein the computer-readable memory stores instructions executable by the one or more processors to determine whether the selected one of the visible numbers comprises two or more digits by determining whether the selected one of the visible numbers is wider than a predetermined maximum digit width value.

9. The supplemental device according to claim 1, wherein two or more numbers having the greatest height are of equal height, and wherein selecting one of the visible numbers to be identified comprises selecting an uppermost of the two or more numbers of equal height.

10. The supplemental device according to claim 7, wherein values for an expected height and an expected width of the numbers visible in the image are pre-programmed in the supplemental device.

11. The supplemental device according to claim 10, wherein the computer-readable memory stores instructions executable by the one or more processors to use the expected width for a number to predict a point or points at which the separation of the two or more digits should occur.

12. The supplemental device according to claim 1, wherein the computer-readable memory stores instructions executable by the one or more processors to cause a value corresponding to a result of an application of a weighting function to the value of the selected number to be displayed on a display of the supplemental device.

13. The supplemental device according to claim 1, wherein the computer-readable memory stores instructions executable by the one or more processors to cause a quality of the data representing the image to be assessed and improved.

14. The supplemental device according to claim 13, wherein assessing and improving the quality of the data representing the image comprises defective and bad pixel correction, light correction and distortion and slant correction.

15. The supplemental device according to claim 1, wherein the computer-readable memory stores instructions executable by the one or more processors to:
   determine that a confidence level of a result of the pattern matching process is below a threshold level; and
   in response to determining that the confidence level is below the threshold level, perform a second pattern matching process on another one of the visible numbers in the image.

16. The supplemental device according to claim 1, wherein the computer-readable memory stores instructions executable by the one or more processors to cause a determined dose value to be displayed, wherein the determined dose value does not correspond to any of the one or more numbers present on the moveable component of the injection device.

17. A system comprising:
   a supplemental device for attachment to an injection device, the supplemental device comprising:
      an imaging sensor configured to capture an image of one or more numbers displayed on a moveable component of the injection device;
      one or more processors;
      a computer-readable memory storing instructions executable by the one or more processors to:
         receive data representing an image;
         determine a position of at least one number in the image by determining one or more boundaries of each visible number;
         select one of the visible numbers to be identified, wherein selecting one of the visible numbers to be identified comprises selecting the number having a greatest height;
         perform a pattern matching process to identify a value of the selected number; and
         determine a dose dialed into the injection device using the determined position of the at least one number in the image; and
   the injection device including the moveable component with numbers present thereon.

18. The system according to claim 17, wherein only even numbers are present on the moveable component.

19. A method of determining a dose dialed into an injection device using a supplemental device for attachment to the injection device, the method comprising:
- receiving a captured image of one or more numbers present on a moveable component of the injection device;
- receiving data representing an image;
- determining a position of at least one number in the image by determining one or more boundaries of each visible number;
- selecting one of the visible numbers to be identified, wherein selecting one of the visible numbers to be identified comprises selecting the number having a greatest height;
- performing a pattern matching process to identify a value of the selected number; and
- determining a dose dialed into the injection device using the determined position of the at least one number in the image.

20. The method according to claim 19, wherein using the determined position of the at least one number to determine the dose dialed into the injection device comprises:
- determining a position offset of the selected number from a center of the image; and
- applying a weighting function based on the position offset to the value of the selected number.

* * * * *